United States Patent
Zapata et al.

(10) Patent No.: US 11,467,389 B2
(45) Date of Patent: Oct. 11, 2022

(54) CONFINED FIELD OF VIEW ILLUMINATION

(71) Applicant: Gentex Corporation, Zeeland, MI (US)

(72) Inventors: Jorge Zapata, Chagrin Falls, OH (US); Carlos Eduardo Vargas Silva, Antioquia (CO)

(73) Assignee: GENTEX CORPORATION, Zeeland, MI (US)

( * ) Notice: Subject to any disclaimer, the term of this patent is extended or adjusted under 35 U.S.C. 154(b) by 846 days.

(21) Appl. No.: 16/387,977

(22) Filed: Apr. 18, 2019

(65) Prior Publication Data

US 2019/0324253 A1 Oct. 24, 2019

Related U.S. Application Data

(60) Provisional application No. 62/659,221, filed on Apr. 18, 2018.

(51) Int. Cl.
*G06K 9/00* (2022.01)
*G02B 21/06* (2006.01)
(Continued)

(52) U.S. Cl.
CPC .............. *G02B 21/06* (2013.01); *A61B 90/30* (2016.02); *G02B 21/0012* (2013.01);
(Continued)

(58) Field of Classification Search
CPC . G06T 7/251; G06T 2207/10016; G06T 7/11; G06T 7/194; G06T 7/215;
(Continued)

(56) References Cited

U.S. PATENT DOCUMENTS

| 4,884,008 A | 11/1989 | Bossler et al. |
| 6,880,957 B2 | 4/2005 | Walters |

(Continued)

FOREIGN PATENT DOCUMENTS

| WO | 2007034796 A1 | 3/2007 |
| WO | 2015/052965 A1 | 4/2015 |
| WO | 2016138063 A1 | 9/2016 |

OTHER PUBLICATIONS

PCT International Search and Written Opinion of the International Searching Authority for Report corresponding PCT/US2019/028074, dated Jul. 30, 2019, pp. 1-12.

*Primary Examiner* — Alex Kok S Liew
(74) *Attorney, Agent, or Firm* — Price Heneveld LLP; Brian James Brewer (57) ABSTRACT

One or more techniques and/or systems are disclosed for effectively illuminating a target. The target may be in a confined field of view area. Such systems may mitigate shadows and lack of light homogeneity at surgical procedure settings, research sites, or other localized areas where humans may operate in a confined field of view area. One or more lighting modules can be disposed in a target area, for illumination of one or more illumination target locations in the confined field of view. An object detection component can detect an object or desired target in the target field of view location, and provide data indicative of the detected object/target to an illumination module adjustment component. Based on the data indicative of the detected object/target, the illumination module adjustment component can provide data indicative of an illumination adjustment to the first illumination module to provide desired illumination.

16 Claims, 5 Drawing Sheets

(51) Int. Cl.
*G06T 7/90* (2017.01)
*G06T 7/00* (2017.01)
*G06T 7/70* (2017.01)
*G02B 21/36* (2006.01)
*A61B 90/30* (2016.01)
*G02B 21/00* (2006.01)
*G06V 10/22* (2022.01)
*G06V 10/141* (2022.01)

(52) U.S. Cl.
CPC .......... *G02B 21/365* (2013.01); *G06T 7/0012* (2013.01); *G06T 7/70* (2017.01); *G06T 7/90* (2017.01); *G06V 10/141* (2022.01); *G06V 10/22* (2022.01); *G06T 2207/10056* (2013.01); *G06T 2207/30004* (2013.01); *G06V 2201/03* (2022.01); *G06V 2201/07* (2022.01)

(58) Field of Classification Search
CPC ... G06T 2207/10036; G06T 7/90; G06T 5/50; G06T 7/32; G06T 7/33; G06T 13/20; G06T 17/00; G06T 19/006; G06T 7/20; G06T 2200/04; G06T 2207/10012; G06T 7/10; G06T 7/248; G06T 7/254; G06T 7/262; G06V 10/141; G06V 10/25; G06V 10/40; G06V 10/751; G06V 20/64; G06V 40/107; G06F 3/017; G06F 3/0304
See application file for complete search history.

(56) References Cited

U.S. PATENT DOCUMENTS

| | | |
|---|---|---|
| 7,573,635 B2 | 8/2009 | Uhl |
| 7,817,335 B2 | 10/2010 | Ryu et al. |
| 8,040,597 B2 | 10/2011 | Sasaki |
| 8,292,804 B2 | 10/2012 | Marka et al. |
| 9,110,288 B2 | 8/2015 | Kaneki et al. |
| 9,119,668 B2 | 9/2015 | Marka et al. |
| 9,491,835 B2 | 11/2016 | Elfring et al. |
| 9,587,804 B2 | 3/2017 | Chen |
| 9,955,551 B2 | 4/2018 | Spero |
| 10,240,751 B2 | 3/2019 | Zapata |
| 2002/0159146 A1 | 10/2002 | Leimbach et al. |
| 2007/0076983 A1* | 4/2007 | Doerrer ................ G02B 21/367 382/128 |
| 2010/0177185 A1* | 7/2010 | Woerlein ............... A61B 90/36 382/128 |
| 2011/0211056 A1* | 9/2011 | Publicover ........... H04N 5/2354 348/78 |
| 2014/0368904 A1 | 12/2014 | Moertelmaier et al. |
| 2016/0174817 A1 | 6/2016 | Frimer et al. |
| 2017/0172662 A1 | 6/2017 | Panescu et al. |
| 2017/0304007 A1 | 10/2017 | Piron et al. |

* cited by examiner

CONFINED FIELD OF VIEW ILLUMINATION

RELATED APPLICATIONS

This application claims priority to U.S. Provisional Ser. No. 62/659,221 titled CONFINED FIELD OF VIEW ILLUMINATION, filed Apr. 18, 2018, which is incorporated herein by reference.

BACKGROUND

An optical microscope utilizes visible light to illuminate a target object within a confined field of view. These and other confined fields of view often utilize an illumination source to provide the visible light that illuminates the target object for desired viewing. Some confined fields of view, which often utilize some sort of magnification, may be used to manipulate the target object at a miniature scale, such as in clinical settings, research settings, manufacturing, etc. In these situations, for example, operating or manipulating object within or adjacent to the field of view may produce reduced illumination, such as resulting from shadows and other sources of lighting distortion, for example, due to fixed illumination types and sources/locations. The current state of the art of illuminating systems demonstrates an inability to eliminate shadows, reflections, and other sources of lighting distortion at confined scenes field of view without instrumentation activity or object manipulation over or around an illumination target.

SUMMARY

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

One or more techniques and systems described herein can be utilized to improve confined field of view (FOV) scene illumination, which may be impacted by obstruction, distortion and any other source of interference to illumination homogeneity of the FOV. For example, systems and methods of illumination, described herein, can utilize an array of light sources grouped in configurable modules to dynamically accommodate specific needs of a confined scene FOV where illumination is used.

In an example implementation, a system for illuminating a target, may comprise a first illumination module that directs light toward a target location in a field of view area; an image recognition subsystem that establishes, based on confinement parameters, a confined field of view area comprising the target location, and detects an object in the confined field of view area; and a motion control subsystem that receives data indicative of the detected object in the confined field of view area from the image recognition subsystem, and transmits data indicative of an illumination adjustment to the first illumination module, the data indicative of an illumination adjustment based upon the data indicative of the detected object in the confined field of view area.

In an example implementation, the first illumination module may comprise a plurality of light sources.

In an example implementation, the system may further comprise a second illumination module that may comprises a plurality of light sources.

In an example implementation, the system may further comprise an optical detection device, wherein the optical detection device is a surgical microscope, and the confinement parameters are determined based on optical parameters of the surgical microscope.

In an example implementation, the confinement parameters may comprise physical boundaries comprising at least one of: line of sight constraints, or surgical microscope magnification area constraints.

In an example implementation, the confinement parameters may comprise optical detection device constraints comprising at least one of: a number of pixels, image size, optical absorption, color depth, or response time.

In an example implementation, the image recognition subsystem may comprise an optimizer subsystem having predictive logic that predicts a future location of the object detected in the confined field of view area, and the data indicative of the illumination adjustment is based on the predicted future location of the object.

In an example implementation, the predictive logic may provide a prediction of light interference based on the future location of the object.

In an example implementation, the data indicative of an illumination adjustment may comprise at least one of: brightness adjustment data, wavelength adjustment data, polarization adjustment data, or focal point adjustment data.

In an example implementation, a method for illuminating a target, may comprise: directing light, by a first illumination module, toward a target location in a field of view area; establishing, by an image recognition subsystem and based on confinement parameters, a confined field of view area within the field of view comprising the target location; detecting, by the image recognition subsystem, an object in the confined field of view area; and transmitting, by the image recognition subsystem to a motion control subsystem, data indicative of the detected object; and transmitting, by the motion control subsystem, data indicative of an illumination adjustment to the first illumination module, the data indicative of the illumination adjustment based upon the data indicative of the detected object in the confined field of view area; and directing the light, by the first illumination module, toward the target location in the confined field of view area based on the received data indicative of the illumination adjustment.

In an example implementation, the confinement parameters comprise physical boundaries comprising at least one of: line of sight constraints, or surgical microscope magnification area constraints.

In an example implementation, the confinement parameters may comprise optical detection device constraints comprising at least one of: a number of pixels, image size, optical absorption, color depth, or response time.

In an example implementation, the method may further comprise predicting, by predictive logic of an optimizer subsystem, a future location of the object detected in the confined field of view area, and the data indicative of the illumination adjustment is based on the predicted future location of the object.

In an example implementation, the predictive logic may provide a prediction of light interference based on the future location of the object.

In an example implementation, the data indicative of an illumination adjustment may comprise at least one of: brightness adjustment data, wavelength adjustment data, polarization adjustment data, or focal point adjustment data.

In an example implementation, a system for illuminating a target, may comprise: a first illumination module that directs light toward a target location in a field of view area; an image recognition subsystem that establishes a confined field of view area comprising the target location based on confinement parameters; an object detection component that detects an object in the field of view area outside the confined field of view area; an optimizer subsystem that predicts formation of light interference in the confined field of view area based on the detected object in the field of view area outside the confined field of view area, and generates illumination adjustment data based on the predicted light interference; and an illumination module adjustment component that receives the illumination adjustment data from the optimizer subsystem, and transmits the illumination adjustment data to the first illumination module.

In an example implementation, the optimizer subsystem may include predictive logic that predicts a future location of the object within the confined field of view area, and the data indicative of the illumination adjustment is based on the predicted future location of the object within the confined field of view.

In an example implementation, the predictive logic may provide a prediction of light interference based on the future location of the object within the confined field of view.

In an example implementation, the confinement parameters may comprise physical boundaries comprising at least one of: line of sight constraints, or surgical microscope magnification area constraints.

In an example implementation, the confinement parameters may comprise optical detection device constraints comprising at least one of: a number of pixels, image size, optical absorption, color depth, or response time.

To the accomplishment of the foregoing and related ends, the following description and annexed drawings set forth certain illustrative aspects and implementations. These are indicative of but a few of the various ways in which one or more aspects may be employed. Other aspects, advantages and novel features of the disclosure will become apparent from the following detailed description when considered in conjunction with the annexed drawings.

DETAILED DESCRIPTION

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are shown in block diagram form in order to facilitate describing the claimed subject matter.

The methods and systems disclosed herein, for example, may be suitable for use in, but not limited to, surgical operating rooms, dental suites, medical intervention rooms, medical examination rooms, laboratories and/or other clinical or otherwise critical human operational confined area that utilizes a uniform light flooding. The methods and system disclosed herein, in a further non-limiting example, may be suitable for use in operations in a confined field of view, such as a microscope or other magnified viewing area, or any other confined field of view susceptible to scene illumination obstruction, distortion, and any other source of interference to illumination homogeneity of the named field of view.

As an example, some of the issues addressed by the methods and system described herein can include, but are not limited to: mitigating shadows or otherwise lack of desired illumination of a target object or location in a confined field of view; simultaneously illuminating a plurality of target objects or areas; creating improved illuminating patterns in real time to account for dynamic interference (e.g., by objects) between the light source and the illuminating target; creating more desirable light wave length pattern in real time, in order to highlight designated illumination targets; and improvement of control objects used to operate illuminations systems.

In one aspect, a system and method of illumination for use in a confined field of view (FOV) may utilize an array of light sources that can be grouped in configurable modules to dynamically accommodate specific needs of a confined scene FOV where illumination is used. In one implementation, the configured modules can work in scalable tandem. In this implementation, the number of modules used in each system may be a function of the nature of the illumination called for in a certain situation. Further, the characteristics of the FOV where the illumination target or plurality of targets are located, the type of operation, and other factors may influence the type and number of modules. As one example, the modules could be located at a gantry or support, surrounding the target object in the FOV (e.g., at a fixed or configurable height), providing illumination for the scene FOV or parts thereof of the designated FOV to be illuminated. In this example, the modules could be arranged such that the illumination target or plurality of illumination targets can be directly illuminated.

In one implementation, the one or more light array modules can comprise of a plurality of light sources that are respectively configurable. In this implementation, respective modules and/or each of the plurality of light sources may be able to be set (e.g., programmed, or otherwise configured) with a unique identifier, such as by the system, in the form of an address or some other identification. Further, respective light sources can be configured to automatically adjust its illuminating properties and/or direction of illumination by changing a target point in space in the FOV. As an example, the target point in space (e.g., its aim point) may be adjusted in a plurality of ways, including, but not limited to, changing axis values (e.g., in the x, y and z axes) or otherwise polar coordinates with reference to a known point in space called home. As an example, the target point can comprise the location in three-dimensional space (e.g., or location on a plane) that the illumination scene FOV is effectively illuminating for the desired operation and FOV characteristics.

In one implementation, a control system can manage a plurality of lights sources respectively configured in each system according to desired settings, such as programmed by a user, or provided by automatic pre-loaded parameters (e.g., for known situations). In one implementation, these settings can be updated dynamically (e.g., in real-time) during an illumination session either manually or automatically as desired and programmed by the user. In one implementation, the management of the illumination sources can be accomplished by the user issuing control commands to the system via visually, auditory, touch, or otherwise electromagnetically recognizable inputs.

In an implementation, automatic management of the plurality of light sources may be accomplished by a control system using an autonomous optimizer algorithm. The optimizer algorithm may find paths between inputs and outputs, thresholds and limitations, and other parameters individually at the respective light sources and/or of a totality of light array modules and individual light sources available in the system.

As an illustrative example, during a designated illumination session, and if programmed by the user, the system could dynamically optimize respective individual light source illuminating properties, and/or direction, dynamically as function of the location and position of a designated illumination target or targets and the relationship with current or potentially obstructing or distortion inducing objects. That is, for example, as the target object or location on the target object is manipulated the illumination properties and/or direction can adjust automatically to accommodate the situation (e.g., to provide desired illumination quality).

In one implementation, the example system can also provide desired illumination properties (e.g., optimal illumination for the situation) of the scene FOV by function of the identified illumination distortion or lack of illumination homogeneity. That is, for example, if an undesired illumination property is detected in the scene FOV the system may automatically adjust the illumination properties to improve the illumination properties, to meet desired quality.

Alternatively, in one implementation, a user could setup an initial target or plurality of targets for illumination and render the system settings static at least until otherwise programmed, or until the illumination session ends. In one implementation, in the event of failure, malfunction or unanticipated behavior during an active illuminating session, the system can be configured to default to a static mode, and can illuminate an entire scene FOV with available light sources, at least until the session ends or it is terminated.

In one implementation, one or more individual light sources can be disposed in respective configurable modules. In one implementation, the distributed nature, type, and size of respective light sources, and their arrangement in the modules can provide for a customizable setup. For example, depending on the use situation, the installation and setup can be customized to mitigate interference with the microscope or other FOV viewing device used for visualization of a target object. In this example, the configuration of the module(s) can mitigate illumination interference by the presence of object, such as furniture, equipment and otherwise large and bulky objects. In another example, the configuration of the module(s) and/or individual light sources may mitigate illumination interference by the presence, or potential presence of an object, in a confined field of view. In a non-limiting example, the object may be an object of a size that would interfere with a magnified confined field of view area.

In one implementation, the example illuminating system can provide sensory feedback to a user, such as by the means of predetermined sound pattern, and/or by a visual user interface, which can also provide control commands, history logs, command acknowledgements, as well as with current system status and upcoming events, amongst other things.

In one implementation, an exemplary illumination system, and/or method of illumination, can comprise a light source array, a control system, a user feedback subsystem, and communication component(s) that may be able to communicate with other devices and/or networks outside the system. As an example, the light source system can comprise one or more configurable modules that are respectively comprised of individual light sources. In this example, respective light sources may have individual motion control and actuators. Further, in this implementation, the control system can comprise an image recognition subsystem (IRS), a motion control, an optimizer subsystem, and/or a logger subsystem.

In one implementation, the IRS can visualize a field of view (FOV), and can create zoning for the FOV utilizing the area of light incidence of the illumination array. As an example, upon activation, the IRS can dynamically analyze the FOV for object motions at the FOV plane, and at planes parallel between the FOV and Illumination array, and combine this information with detected changes in illumination of any target objects in the FOV plane. In this example, based on IRS data, a position optimizer can produce updated light configuration parameters for lights configured within the light array.

Figure 1:
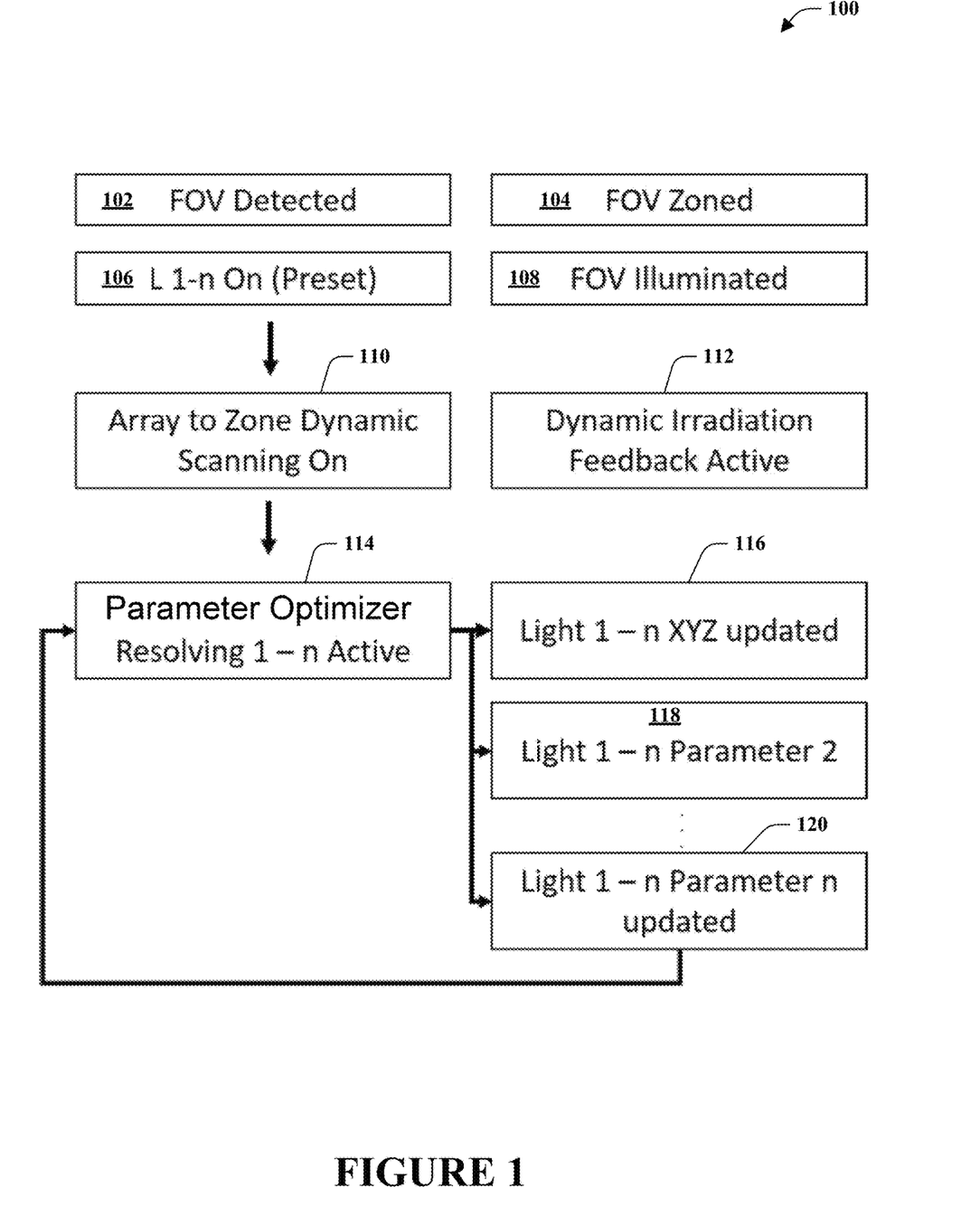
FIG. 1 is a flow diagram illustrating an example implementation of one or more portions of one or more techniques described herein.

As an illustrative example, a depiction of the process for dynamic FOV processing is described in FIG. 1. As illustrated in the exemplary technique 100, the field of view (FOV) can be detected, at 102, for example, visualized by the IRS. The field of view may include a target area and/or an object or potential object (e.g., an object that may potentially enter the FOV). The field of view may be constrained. For example, the field of view may be constrained by physical boundaries (e.g., line of sight, or a surgical microscope magnification area). The field of view may also be constrained by the optical detection device (e.g., camera) parameters. For example, the optical detection device may be constrained by the number of pixels, image size, optical absorption, color depth, response time, and the like. Parameters associated with respective constraints may be stored and used by the system as confinement parameters, for example, by the optimization algorithm. A confined field of view may be established based on the constraint parameters. In an example, the confined field of view may be a subset of the overall field of view. In a further example, the confined field of view may include multiple, non-overlapping, subsets of the overall field of view.

In an example implementation, the system may further comprise an optical detection device used in laparoscopic surgeries, and the confinement parameters may be based on the optical parameters of the optical detection device, and the inner body environment is used.

Figure 2:
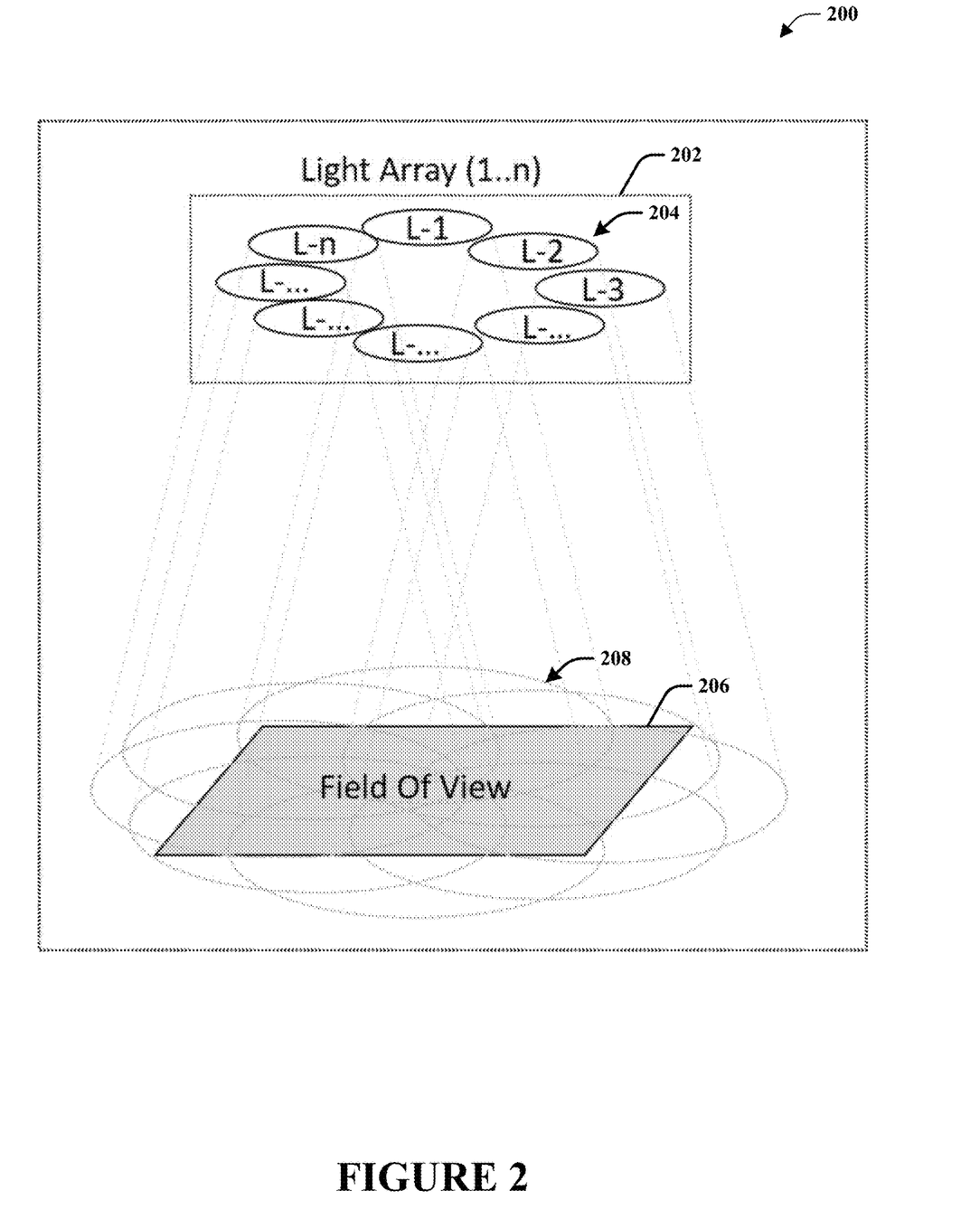
FIG. 2 is a component diagram illustrating an example implementation of one or more techniques and/or one or more systems described herein.

At 104, the zoning for the FOV can be created. As an illustrative example, as illustrated in the example implementation 200 of FIG. 2, a light array 202 can be configured with one or more light modules 204. In this example, respective light modules 204 can be configured to provide illumination to a pre-determined zone 208, for example, based at least upon the light array configuration and the geometry of the FOV 206, such as created in the zoning (e.g., 104 of FIG. 1).

Returning to FIG. 1, at 106, the light array (e.g., 202) comprising light modules L1-Ln (e.g., 204) can be powered on to a preset configuration, providing illumination to the FOV, at 108. At 110, a dynamic scanning operation can be commenced by the array, for example, using respective zones (e.g. 208) and FOV (e.g., 206). In one implementation, based on dynamic irradiation feedback activated, at 112, from objects or targets located in the FOV the dynamic scanning operation can provide data indicative of an illumination optimization for the situation detected in the FOV. For example, one or more objects in the FOV may create dim zones (e.g., created by shadows) in the FOV based on their orientation with respect to the one or more light modules. Therefore, in this example, the dynamic (e.g., in real-time) feedback from the FOV irradiation can provide data that may be used to mitigate dim areas in the FOV, and provide a desired amount and type of illumination for the desired task.

Figure 3:
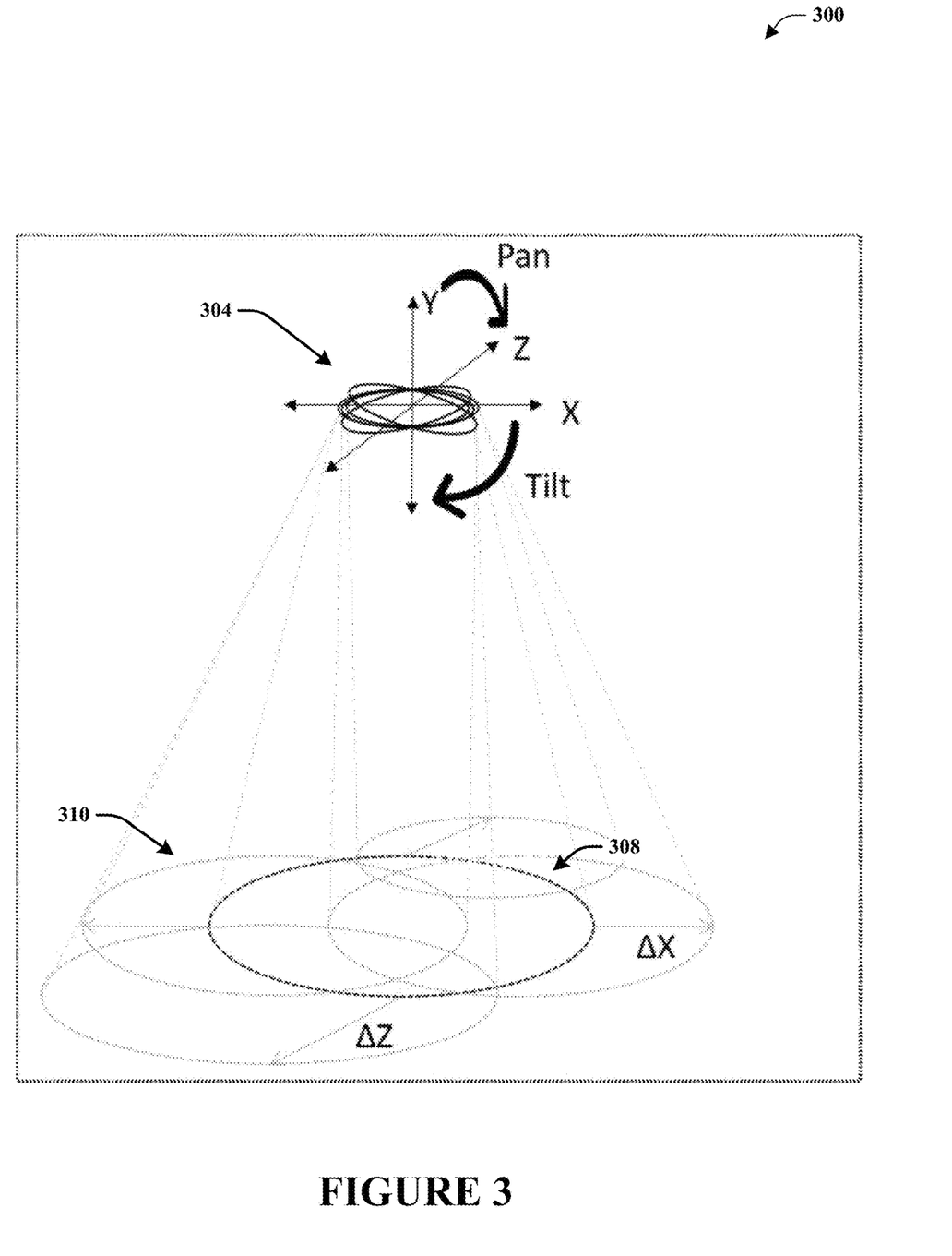
FIG. 3 is a component diagram illustrating an example implementation of one or more techniques and/or one or more systems described herein.

A an illustrative example, as illustrated in FIG. 3, respective light modules 304 can be configured with motion control and actuators that enable light beam change of incidence area in orthogonal axis at the FOV. In this illustrative example, 300, a base illumination zone 308 may be adjusted to alternate illumination zones 310, based at least on a panning and/or tilting of the light module 304, thereby resulting in a change in irradiation incidence at the FOV. Returning to FIG. 1, at 114, a position optimizer (e.g., optimizer subsystem) can resolve 1-*n* active light modules (e.g., 204) for the respective light arrays.

The optimizer subsystem may, for example, include an optimizing algorithm. In a non-limiting example, the optimizing algorithm may be generated (e.g., trained) by a machine learning process in a controlled environment, where the algorithm is improved and optimized over a period of time. In a further example, the optimizing algorithm of the optimizing subsystem may be configurable and may be changed and/or updated (e.g., based on environmental, geometric, or performance requirements).

The optimizer algorithm may further include predictive logic such that the dynamic scanning data may be used to predict a future location of an object within the confined field of view. For example, dynamic scanning data may provide multiple reads of a moving object or objects. The predictive logic of the optimizer algorithm may provide predictions of light interference in advance of actual interference detection within the confined field of view. Such advance light interference may correspondingly be proactively corrected with adjustment data that may be sent from the optimizer subsystem to the respective light module(s).

In a further example implementation, the predictive logic may be used in a non-physical confined setting by simulating a constraint mathematically to a defined area of a field of view that is smaller than the actual field of view of the optical detection device (e.g., cameras).

Turning back to FIG. 1, as a result of a determined adjustment (e.g., from the optimizer subsystem), at 116, light modules 1-*n* can have their respective X, Y, and Z axes adjusted, accordingly. At 118, light modules 1-*n* can have their respective second parameter's (e.g., brightness) adjusted, accordingly. At 120, light modules 1-*n* can have their respective n parameters' (e.g., brightness, color, wavelength, polarization, focal point, etc.) adjusted, accordingly. This process can iterate at 114, at least until optimization is no longer needed, and/or the operation in the FOV has completed.

Figure 4:
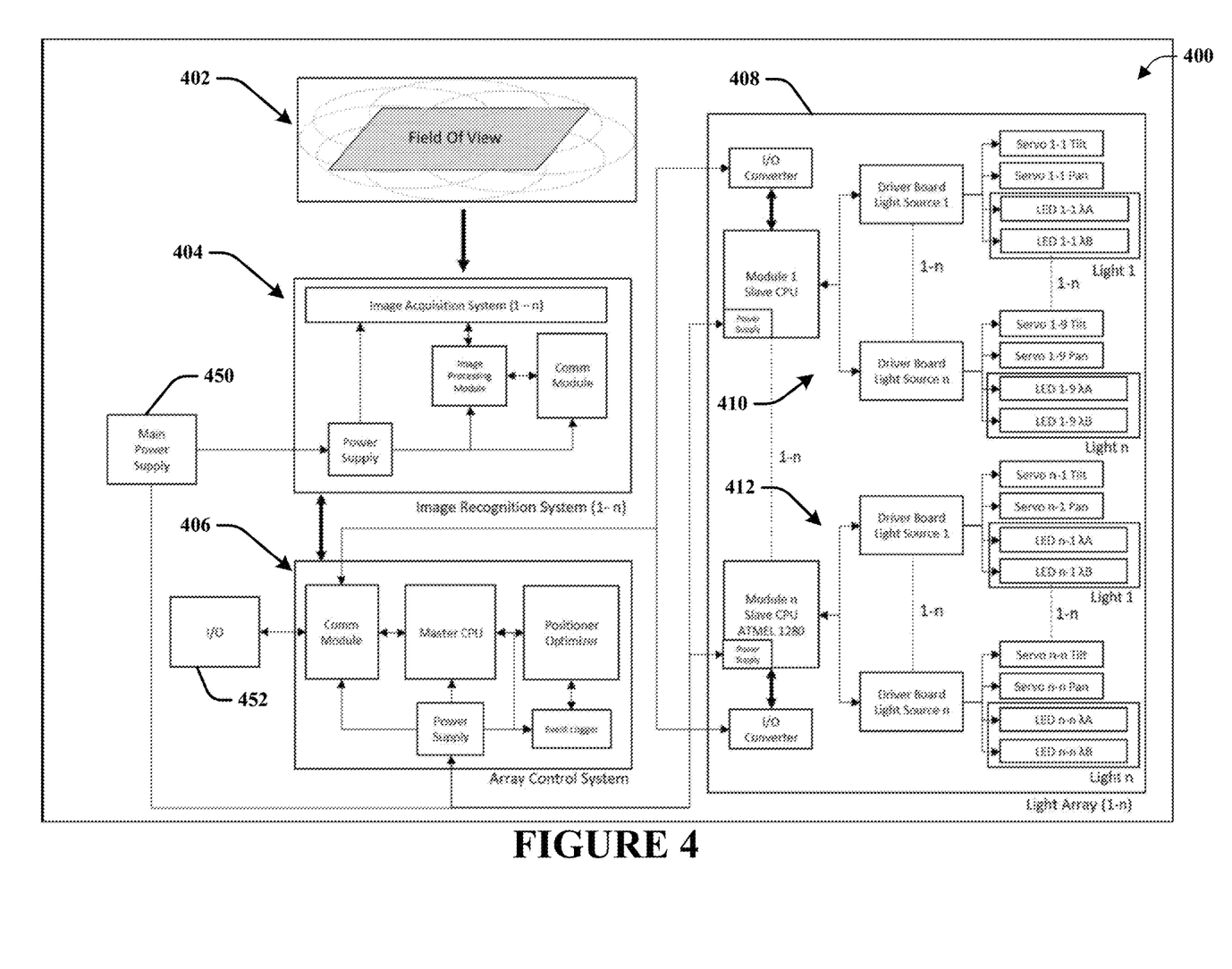
FIG. 4 is a schematic diagram illustrating an example implementation of one or more portions of one or more systems described herein.

In one aspect, an illumination system, such as described herein, can be modular and scalable. For example, a modular and scalable illumination system could be used to illuminate FOV of various sizes and characteristics, and comprising various operations. FIG. 4 is a schematic diagram illustrating one implementation of an example illumination system 400 that may be modular and scalable. In this example, system 400, a main power supply 450 can provide power (e.g., electrical) to one or more modular components (e.g., subsystems), such as an image recognition component 404, and an array control component 406. As described above, and as illustrated, the image recognition component 404 may receive feedback (e.g., images, data, irradiation, etc.) from the field of view 402 comprising a target operation/object/target. As an example, the feedback can be used to generate data used to adjust the respective light modules to produce a desired illumination for the target area. In this example implementation 400, the image recognition component 404 can comprise an image acquisition component, such as for respective 1-*n* light modules; an image processing module, for processing images; and a communication module, for communicating with one or more other components.

Further, in the example, system 400, the array control component 406 can be configured to provide data, power and other signals to control the one or more light modules. As an example, the image recognition component 404 can provide data indicative of one or more characteristics of the field of view 402, such as target objects, irradiation, locations of objects, vectors, etc. to the array control component 406. In this example, the data indicative of one or more characteristics of the field of view 402, in combination with input data provided from a used input/output component 452, can be used to control the one or more light modules 408. In this implementation, the array control component 406 can comprise a communication module, for communicating with one or more other components; a master processor, for processing data; a position optimizer (e.g., an optimizer subsystem including optimizing algorithm(s)), for generating data indicative of optimized illumination in the FOV 402, and an event logger, for collecting and logging event data. In one implementation, the input/output component 452 can be used to receive input from a user, where the input is indicative of instructions for the exemplary system 400, and/or provide output, such as visual and/or auditory indicators, to the user of system information.

As illustrated in the example implementation, the exemplary system 400 can comprise one or more light modules 408. For example, a set of light modules 408 can comprise a first light module 410, and n additional light modules 412 (e.g., one or more additional modules). As an example, n sets of light modules 412 can be utilized in the exemplary system 400, and the actual number, location, type and size may be dependent on the situation where the confined field of view is expected to be used, the type of operation conducted, and/or the type of illumination characteristics desired.

In this implementation, respective light modules 410, 412 can comprise a CPU, with a power supply to process data (e.g., operation instructions); and an I/O converter, to receive data and transmit responsive data. Further, respective modules can comprise one or more driver boards, for providing instructional signals and/or power to respective individual light arrays; one or more light arrays, respectively coupled with an actuator, such as a servo to adjust the light source (e.g., pan and/or tilt), to provide the desire illumination to the field of view 402. Further in this implementation, respective light modules 410, 412 may be controlled to adjust brightness, color, wavelength, polarization, focal point, and the like of the light module as whole or by control of individual light sources.

This system and method of illumination is applicable to address scene illumination obstruction, shadows, distortion and any other source of interference to illumination homogeneity of the named scene FOV. It is applicable to address the inability of simultaneously illuminating a plurality of illuminating targets. This invention is applicable when is desirable to optimize illuminating patterns in real time to account for instruments use or other objects dynamic interference between the light source and the illuminating target. It is also applicable to address aseptic requirements of control objects required to operate luminaries and illuminations and control systems.

This invention is applicable but not limited to illuminating microscopic surgical sessions at surgical operating rooms or any microscope use settings. It is also applicable to illuminate desktop laboratories procedures and practices at clinical, chemical and other laboratory settings. It is also applicable to workbench engineering, manufacturing and machinery and repair shops settings that are prone of illumination interference due to their own configuration, motion of instruments and objects and human manipulation or movement. It is also applicable to any illumination setting that benefits from removing the need to touch or otherwise physically interact with the illumination device.

Figure 5:
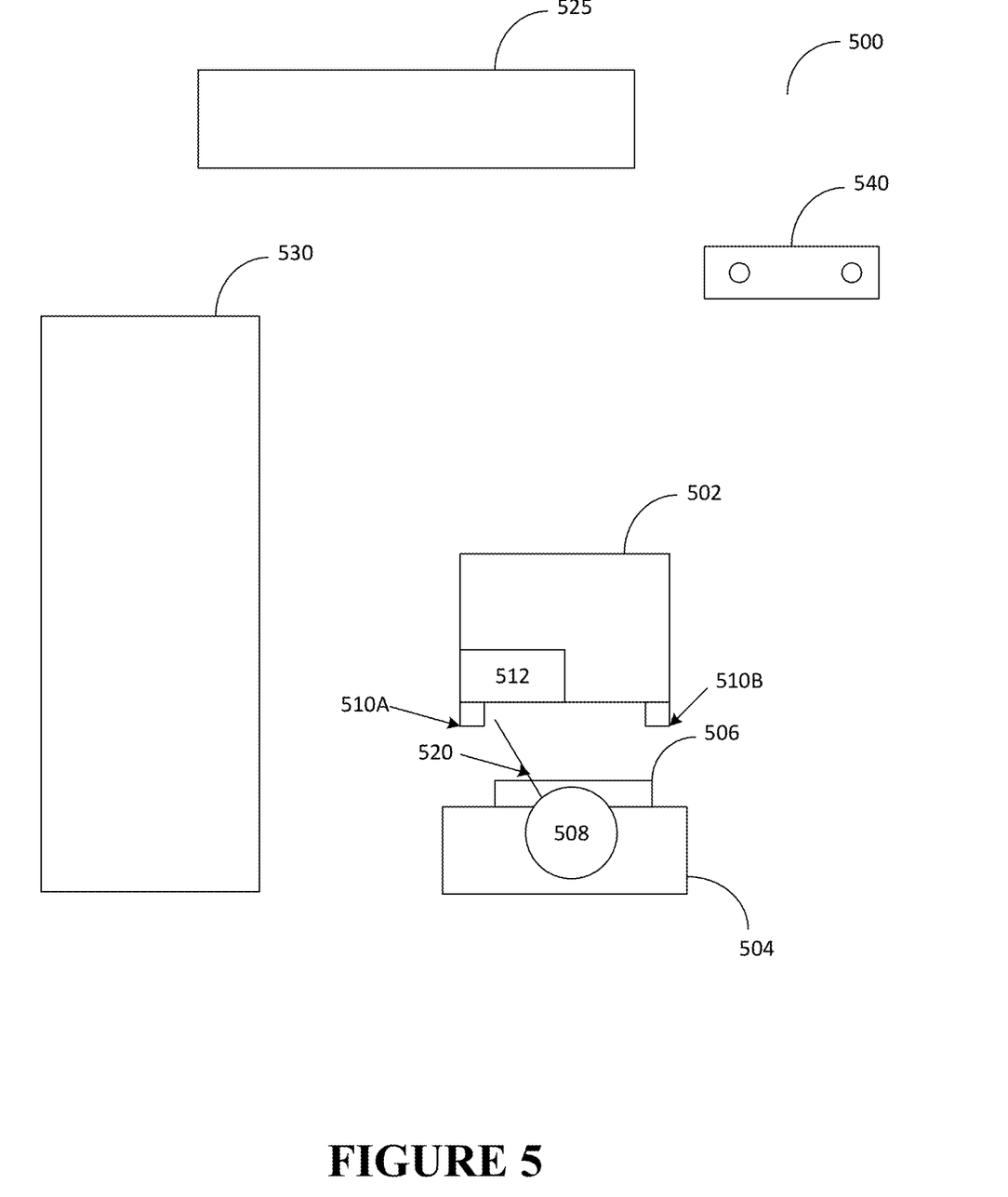
FIG. 5 is a block diagram illustrating an example implementation of one or more portions of one or more systems described herein.

FIG. 5 illustrates a non-limiting example environment 500. Components of the environment are for reference and not shown to scale. For example, the environment may be an operating room. The operating room contains first medical equipment 502. For example, the medical equipment 502 may be an optical detection device, for example, a surgical microscope. The surgical microscope has a field of view 504. The surgical microscope 502 also has a confined field of view 506. The confined field of view 506 is smaller than the field of view 504. The confined field of view may be established based on confinement parameters based on, for example, the surgical microscope 502, as discussed in more detail earlier above.

A target 508 (e.g., a part of a body of a patient) is located within the field of view 504 and the confined field of view 506. A surgeon (not shown) may use the microscope to create a magnified view of a portion of the target 508.

The operating room has general lighting 525. General lighting 525 illuminates the room including the target 508, the field of view 504, and the confined field of view 506. Illumination distortions will be created in the field of view 504 and the confined field of view 506 due to shadows, reflections, interference, and other illumination distortions as discussed in greater detail above. For example, second medical equipment 530 may create shadows or reflections from light incident from general lighting 525. Second medical equipment 530 may be a gantry or other medical device, for example.

A dynamic lighting control system 512 and light modules 510A and/or 510B (e.g., system 400 as described in greater detail earlier), may be used to alleviate illumination distortions in images taken by the surgical microscope 502 as well as images taken by an external optical system 540. External optical system 540, for example, may be a stereoscopic camera that is part of a medical navigation system. Two light modules 510A and 510B are illustrated in this non-limiting example, but, a single light module (e.g., 510A or 510B) may also be used. In further examples, more than two light modules may be used (e.g., n modules may be employed). Further, the light modules 510A and 510B are shown as located on or adjacent to the surgical microscope 502. But any light module combination—namely, single, multiple, plural, may be located at any location in the environment 500 that allows for at least partial line of sight to the target 508 and the field of view 504 and confined field of view 506.

In an example, an object 520 may be introduced into the field of view 504 and/or the confined field of view 506 near object 508. The object 520 may be, for example, a surgical instrument (e.g., a navigation pointer). Introduction of the object 520 may cause undesirable changes in the lighting of target 508. For example, introduction of the object 520 may cause shadows, reflections, interference, and/or other illumination distortions as discussed in greater detail earlier. To correct for these illumination distortions, dynamic lighting control system 512 and light modules 510A and/or 510B may be used, for example, as described in example technique 100 described in greater detail above. As discussed earlier, such correction by dynamic lighting control system 512 and light modules 510A and/or 510B may be done automatically or manually by, for example, the surgeon.

As discussed in greater detail earlier, correction by dynamic lighting control system 512 and light modules 510A and/or 510B may be predictive. For example, correction of potential illumination distortions may be pre-empted by dynamic lighting control system 512 and light modules 510A and/or 510B by predicting illumination distortions caused by movement of the object 520 into confined field of view 506 from field of view 504. Other predictive aspects may be made by utilization of previously captured images by surgical microscope 502 and/or external optical system 540 to create a time-based progression using, for example, the predictive logic of the optimizer system, as discussed in greater detail earlier.

The word "exemplary" is used herein to mean serving as an example, instance or illustration. Any aspect or design described herein as "exemplary" is not necessarily to be construed as advantageous over other aspects or designs. Rather, use of the word exemplary is intended to present concepts in a concrete fashion. As used in this application, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Further, At least one of A and B and/or the like generally means A or B or both A and B. In addition, the articles "a" and "an" as used in this application and the appended claims may generally be construed to mean "one or more" unless specified otherwise or clear from context to be directed to a singular form.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used in this application, the terms "component," "module," "system," "interface," and the like are generally intended to refer to a computer-related entity, either hardware, a combination of hardware and software, software, or software in execution. For example, a component may be, but is not limited to being, a process running on a processor, a processor, an object, an executable, a thread of execution, a program and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus or article of manufacture using standard programming and/or engineering techniques to produce software, firmware, hardware or any combination thereof to control a computer to implement the disclosed subject matter. The term "article of manufacture" as used herein is intended to encompass a computer program accessible from any computer-readable device, carrier or media. Of course, those skilled in the art will recognize many modifications may be made to this configuration without departing from the scope or spirit of the claimed subject matter.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes," "having," "has," "with," or variants thereof are used in either the detailed description or the claims, such terms are intended to be inclusive in a manner similar to the term "comprising."

The implementations have been described, hereinabove. It will be apparent to those skilled in the art that the above methods and apparatuses may incorporate changes and modifications without departing from the general scope of this invention. It is intended to include all such modifications and alterations in so far as they come within the scope of the appended claims or the equivalents thereof.

What is claimed is:

1. A system for illuminating a target, comprising:
   a first illumination module that directs light toward a target location in a field of view area;
   an image recognition subsystem that establishes, based on confinement parameters, a confined field of view area comprising the target location, and detects an object in the confined field of view area, wherein the image recognition subsystem comprises an optimizer subsystem having predictive logic that predicts a future location of the object detected in the confined field of view area and provides a prediction of a light interference based on the future location of the object; and
   a motion control subsystem that receives data indicative of the detected object in the confined field of view area from the image recognition subsystem, and transmits data indicative of an illumination adjustment to the first illumination module, the data indicative of an illumination adjustment based upon the data indicative of the detected object in the confined field of view area, and the predicted future location of the object, wherein the data indicative of the illumination adjustment comprises a proactive control instruction directing light to illuminate the target location without the light interference based on the future location of the object.

2. The system of claim 1, wherein the first illumination module comprises a plurality of light sources.

3. The system of claim 1, further comprising a second illumination module that comprises a plurality of light sources.

4. The system of claim 1, further comprising an optical detection device, wherein the optical detection device is a surgical microscope, and the confinement parameters are determined based on optical parameters of the surgical microscope.

5. The system of claim 1, wherein the confinement parameters comprise physical boundaries comprising at least one of:
   line of sight constraints, or
   surgical microscope magnification area constraints.

6. The system of claim 1, wherein the confinement parameters comprise optical detection device constraints comprising at least one of:
   a number of pixels,
   image size,
   optical absorption,
   color depth, or
   response time.

7. The system of claim 1, wherein the data indicative of an illumination adjustment comprises at least one of:
   brightness adjustment data,
   wavelength adjustment data,
   polarization adjustment data, or
   focal point adjustment data.

8. A method for illuminating a target, comprising:
   directing light, by a first illumination module, toward a target location in a field of view area;
   establishing, by an image recognition subsystem and based on confinement parameters, a confined field of view area within the field of view comprising the target location;
   detecting, by the image recognition subsystem, an object in the confined field of view area;
   predicting, by predictive logic of an optimizer subsystem, a future location of the object detected in the confined field of view area, and the data indicative of the illumination adjustment is based on the predicted future location of the object;
   transmitting, by the image recognition subsystem to a motion control subsystem, data indicative of the detected object;
   transmitting, by the motion control subsystem, data indicative of an illumination adjustment to the first illumination module, the data indicative of the illumination adjustment based upon the data indicative of the detected object in the confined field of view area; and
   directing the light, by the first illumination module, toward the target location in the confined field of view area based on the received data indicative of the illumination adjustment and the predicted future location of the object, wherein an interference of the object in the future location is mitigated by controlling the first illumination module to illuminate the target location without the interference.

9. The method of claim 8, wherein the confinement parameters comprise physical boundaries comprising at least one of:

line of sight constraints, or surgical microscope magnification area constraints.

10. The method of claim 8, wherein the confinement parameters comprise optical detection device constraints comprising at least one of:

a number of pixels, image size, optical absorption, color depth, or response time.

11. The method of claim 8, wherein the data indicative of an illumination adjustment comprises at least one of:

brightness adjustment data, wavelength adjustment data, polarization adjustment data, or focal point adjustment data.

12. A system for illuminating a target, comprising:

a first illumination module that directs light toward a target location in a field of view area;

an image recognition subsystem that establishes a confined field of view area comprising the target location based on confinement parameters;

an object detection component that detects an object in the field of view area outside the confined field of view area;

an optimizer subsystem that predicts formation of light interference in the confined field of view area based on the detected object in the field of view area outside the confined field of view area, and generates illumination adjustment data based on the predicted light interference; and an illumination module adjustment component that receives the illumination adjustment data from the optimizer subsystem, and transmits the illumination adjustment data to the first illumination module.

13. The system of claim 12, wherein the optimizer subsystem includes predictive logic that predicts a future location of the object within the confined field of view area, and the data indicative of the illumination adjustment is based on the predicted future location of the object within the confined field of view.

14. The system of claim 13, wherein the predictive logic provides a prediction of light interference based on the future location of the object within the confined field of view.

15. The system of claim 12, wherein the confinement parameters comprise physical boundaries comprising at least one of:

line of sight constraints, or surgical microscope magnification area constraints.

16. The system of claim 12, wherein the confinement parameters comprise optical detection device constraints comprising at least one of:

a number of pixels, image size, optical absorption, color depth, or response time.

* * * * *